United States Patent [19]

Osther et al.

[11] Patent Number: 4,885,235

[45] Date of Patent: * Dec. 5, 1989

[54] METHOD FOR RAPID AND SENSITIVE DETECTION OF HIV-1 ANTIBODIES

[75] Inventors: Kurt B. Osther, Dallas; Louis M. Dyll, Rockwall, both of Tex.

[73] Assignee: 501 Bio-Research Laboratories, Inc., Southport, Conn.

[*] Notice: The portion of the term of this patent subsequent to Mar. 28, 2006 has been disclaimed.

[21] Appl. No.: 99,311

[22] Filed: Sep. 21, 1987

[30] Foreign Application Priority Data

Jul. 6, 1987 [DK] Denmark .................... 3622/87

[51] Int. Cl.$^4$ ........................................ G01N 33/569
[52] U.S. Cl. ................................ 435/5; 422/61; 422/70; 435/6; 435/7; 435/28; 435/239; 435/805; 435/810
[58] Field of Search .............. 435/5, 7, 6, 28, 239, 435/805, 810; 422/61, 70

[56] References Cited

U.S. PATENT DOCUMENTS 4,452,901  6/1984  Gordon et al. .
4,520,113  5/1985  Gallo et al. .
4,629,783  12/1986 Cosand .
4,661,445  4/1987  Saxinger et al. .
4,708,818  11/1987 Montagnier et al. .

OTHER PUBLICATIONS

W. Van Raamsdonk, et al., *J. Immunol Methods* 17:337 (1977).
Towbin, et al., Proc. Natl. Acad. Sci. U.S.A. 76:4350-4354 (1979).
V. Tsang, et al., *Methods in Enzymology* 92, 377-391 (1983).
M. Essex, et al., *Science* 220, 859 (1983).
M. G. Sarngadharan, et al., *Science* 224, 506 (1983).
R. Gallo, et al., *Science* 224, 500-503, May 4, 1984.
B. Safai, et al., *Lancet I*, 1438-1440, Jun. 30, 1984.
G. Biberfeld, et al., *Scand, J. Immunol.* 21, 289-292 (1985).
S. Weiss, et al., *JAMA* 253, 221-225, Jan. 11, 1985.
J. Schupbach, et al., *N. Engl. J. Med.* 312, 265-270, Jan. 31, 1985.
J. Carlson, et al., *JAMA* 253, 3405-3408, Jun. 21, 1985.
Geroldi, et al., *Infection* 14, 60-63 (1986).
Cabradilla, et al., *Bio/Technology* 4:128-13, Feb. 1986.
Groopman, et al., *J. Infec. Dis.* 153: 736-742, Apr. 1986.
Johnson, et al., *Gene Angl. Techn* 1:3-8 (1984).

*Primary Examiner*—Christine M. Nucker
*Attorney, Agent, or Firm*—Bryan, Cave, McPheeters & McRoberts

[57] ABSTRACT

A rapid and sensitive assay method for the detection of antibodies to Human T-Cell Leukemia Virus-III (HIV-I), the AIDS virus, and diagnostic test kits for carrying out method. According to the method of the invention, which is referred to as a Quick Western Blot II or Rapid Western Blot, electrophoretically resolved HIV-I anitgen is incubated in the presence of milk proteins.

16 Claims, 1 Drawing Sheet

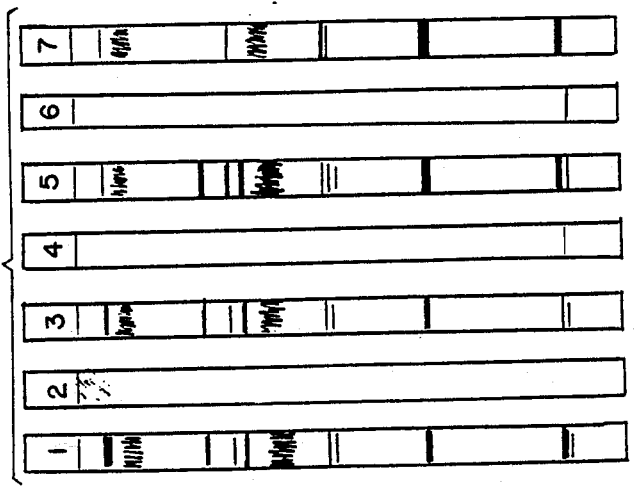
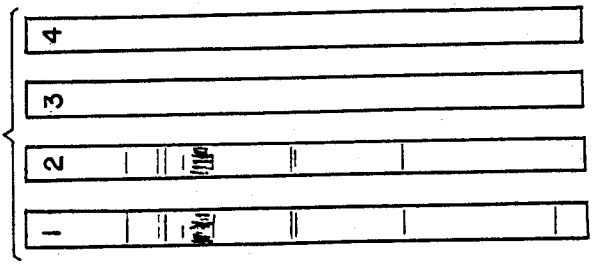

METHOD FOR RAPID AND SENSITIVE DETECTION OF HIV-1 ANTIBODIES

TECHNICAL FIELD

The present invention relates to a rapid and sensitive assay method for the detection of antibodies to Human T-Cell Leukemia Virus-III (HIV-I) antigen, and diagnostic test kits for carrying out the assay method.

BACKGROUND OF THE INVENTION

Acquired immune deficiency syndrome (AIDS) was first recognized in approximately 1981, but the causative agent had not yet been identified. Intense research efforts resulted in the detection and isolation of HIV-I (previously known as HTLV-III/LAV), the retrovirus identified as the etiologic agent of AIDS.

The virus is currently believed to be transmitted through intimate sexual contact and blood. Thus far, epidemiologic evidence indicates that food, water, insects and casual contact are not disease vectors.

The AIDS virus acts by crippling the body's immune system. Particularly, HIV-I selectively attacks T4 lymphocytes, one of the subpopulations of lymphocytes that constitute the immune system. Infection with HIV-I results in both a reduction in the number and a change in the function of the targeted T4 lymphocytes with the eventual collapse of the immune system.

The groups at highest risk of infection with HIV-I include homosexual and bisexual men and abusers of injected drugs. Other predictable high risk groups are women artificially inseminated with sperm from infected donors and sexual partners of those in the AIDS risk groups. Recipients of blood transfusions and blood products are also at risk of contracting AIDS.

Organ transplant recipients are also a high risk group. Recognizing organ transplantation as a potential avenue for the spread of AIDS, testing for HIV-I antibodies is now performed on all organ donors. With the exception of some kidney transplants it is often difficult to predict in advance the source of a donated organ. For example, victims of fatal automobile accidents are potential organ donors, and as the time and place of accidents are not foreseeable, pre-transplant testing presents a problem. Screening is thus difficult in this and similar situations and the need for 24 hour testing facilities and, more importantly, on site testing is apparent. Further, in view of the limited useful life of a donated organ once removed from the host, the need for a rapid assay method is evident.

Present methods for the detection of antibodies to the AIDS virus include the so-called enzyme-linked immunosorbance assay (ELISA), the Western Blot assay and the immunofluorescent assay. Such assays are described in Sarngadharan, M. G. et al., Science 224:506 (1983) (ELISA); Tsang et al., In: Methods of Enzymology, vol. 92, Chapter 29, 1983, Academic Press and Safai, B. et al., Lancet 1:1438 (1984) (Western Blot), and Essex, M. et al., Science 220:859 (1983) (immunofluorescent techniques). The established method for blood donor screening is to first carry out an ELISA, followed by confirmation of positives by Western Blot.

The ELISA technique involves reacting a test sample with an antigen reagent generally obtained from disrupted whole or density-banded HIV-I. Typically, the HIV-I is coated onto wells of a microtiter plate. After washing to remove unbound antibodies, goat-antihuman IgG antiserum conjugated with horseradish peroxidase is added to the wells and incubated. After an appropriate incubation period, an enzyme substrate is added to the mixture and a detectable, measurable color product is formed in the presence of antibodies to HIV-I.

In the Western Blot assay, on the other hand, the HIV-I antigen is electrophoretically resolved on SDS-polyacrylamide gels, each $8 \times 10$ cm gel being loaded with 5–10 ug of protein. The resulting protein bands are electro-transferred to nitrocellulose paper. Detection of antibodies to HIV-I is then carried out by either solid phase strip radioimmunoassay techniques or by ELISA. Each of these methods includes an overnight incubation, and thus, an overall test time of about 20 hours.

The established screening procedure is not entirely satisfactory because of the time required to obtain results. This is particularly true in the organ transplant situation, especially for the heart and liver. These two organs have maximum cold ischemic times of 4 and 8 hours, respectively. Generally, ELISA takes about 4 hours and the Western Blot which, as noted, includes an overnight incubation period, requires about 20 hours. As can be appreciated, with conventional techniques test results would not be obtained within the maximum ischemic times for the heart or liver.

The so-called "Quick Western Blot" assay is a modification of the standard Western Blot assay and is the subject of U.S. patent application Ser. No. 871,505, filed on June 6, 1986 in the name of Kurt B. Osther. The test involves a Western Blot assay wherein the concentration of the sample being tested as well as the HIV-I antigen used is increased by at least 50% over the standard Western Blot. The technique then involves using the ELISA test to detect the bound antibodies. Because of the increased concentration of the antigen and test sample the resultant assay can be accomplished in as little as one hour and twenty minutes without the expected nonspecific protein noise. Furthermore the test can be done in areas not equipped to perform the other more time consuming tests.

Although the Quick Western Blot method is both quick and sensitive, it is an object of the present invention is to provide an even more rapid and sensitive assay for the detection of antibodies to HIV-I.

SUMMARY OF THE INVENTION

The present invention involves a rapid and sensitive method for the detection of antibodies to HIV-I antigen which uses a modified Quick Western Blot technique. Specifically, the method comprises incubating electrophoretically resolved HIV-I antigen protein with a test sample in the presence of milk proteins.

Surprisingly, the milk proteins act to both enhance and accelerate specific protein binding; and to decrease unspecific protein binding. Consequently, test results are obtained in 50–60 minutes.

In the Western Blot assay the serum sample is diluted in order that non-specific binding of other proteins present therein will not produce overlapping protein banding interfering with the detection of antibodies to the HIV-I antigen. On the other hand, employing the Quick Western Blot assay described in the aforesaid Osther application, protein concentrations at least 50% greater than those used in the conventional Western Blot have been successfully employed to detect antibodies to the AIDS virus while decreasing the test time by a factor of ten. It has now been found in accordance with the present invention that, when the HIV-I antigen is incubated in the presence of milk proteins, specific binding of the HIV-I antibody to the antigen is both enhanced and accelerated.

Utilizing the method of the present invention the concentration of the test sample may be increased relative to that used in the Western Blot Assay without impairing the selectivity of the assay, while the concentration of the sample may be decreased relative to that employed in the Quick Western Blot without either impairing the sensitivity or increasing the incubation times required for the assay. Indeed, the assay of the present invention results in better resolution than the Western Blot, enhanced specific binding relative to the Quick Western Blot, and markedly decreased incubation times than required to complete either the conventional Western Blot or Quick Western Blot assays. Furthermore, the assay of this invention produces significantly more distinct protein bands. This is extremely important for the reading of the test strips.

In accordance with the assay procedure, the milk proteins are present when the antibodies of HIV-I, possibly present in the sample to be tested, are reacted with the HIV-I antigen. It is believed that one or more of the milk proteins changes the electronic structure of the binding site on the antigen thereby increasing its affinity and specificity for the HIV-I antibody.

It will be understood that the preceding explanation is a hypothesis based on the limited information currently available, and is subject to revision based on later developments. Accordingly, the present invention is not restricted thereto.

The method of the invention applies blotting techniques but uses at least 20%, preferably about 20% to 40%, more HIV-I viral lysate than conventional Western Blot. In particular, from 60 to about 120 ug of HIV-I antigen protein/10×16 cm gel is used in the method of the invention, as compared with the 50–100ug of protein/10×16 cm gel used in conventional Western Blot. Concentrations of test sample are also increased at least 3 times, preferably about 5 to 7 times, than that used in conventional Western Blot.

The method of the invention, like the conventional Western Blot, employs an electrophoretically resolved antigen subsequently electrotransferred to test sheets or strips. The increase in the antigen concentration of the lysate together with the increased sample concentration and the introduction of milk proteins, facilitate a drastic reduction in incubation times. In accordance with the present method, test results are obtained in 50–60 minutes, that is 1/30 the time required to perform the Western Blot assay and ¾ the time required for the Quick Western Blot assay. The method hereof is, therefore, referred to as the "Quick Western Blot II" technique.

The method involves electrophoretically resolving HIV-I antigen lysate and subsequently electrotransferring the resolved antigen onto nitrocellulose paper. This paper is incubated with the sample to be tested in order to detect any HIV-I antibodies present. The incubation step is performed in the presence of the milk proteins.

The nitrocellulose bound antigen/antibody complex is incubated with enzyme conjugated antiserum and developed with an enzyme substrate (color change indicator). The resultant colored bands are then visually compared with positive and negative controls in order to ascertain the presence of HIV-I antibodies.

In a preferred embodiment of the present invention, a diagnostic test kit is provided which permits on site testing for antibodies to AIDS virus. The kit comprises a set of control tubes for positive and negative references as well as a dilution tube with buffer for dilution of the test sample. The contents of these tubes are added to reaction tubes containing nitrocellulose test strips containing resolved HIV-I antigen and incubated. The resultant strips are incubated with the supplied enzyme conjugated antiserum used to detect whether any bound antibodies are present. The strips are then ultimately developed for color with a color change indicator.

The diagnostic kit of the invention also includes predeveloped positive and negative reference strips and reagent control strips for evaluating the test results by visual comparison with the test strips. The visible protein bands on the test sample strip with the positive reference strip should test positive for HIV-I antibodies (as shown from the prespecified protein bands). The negative reference strip should test negative for the HIV-I antibody. Accordingly, reading the results of the test is facilitated and the need for specially trained personnel is virtually eliminated. On site testing is particularly important in the organ transplant situation because screening for AIDS can now be performed on a 24 hour basis at virtually any location, without specially trained personnel, and test results can be obtained in 50–60 minutes, comfortably within the life span of ischemic organs.

DETAILED DESCRIPTION OF THE INVENTION

Resolution Of The HIV-I Antigen

In accordance with the method of the invention, HIV-I antigen concentrate is electrophoretically resolved. The HIV-I antigen concentrate may be obtained commercially, for example, as from Litton Bionetics as HIV-I viral lysate, Catalog No. 8464–15. The antigen concentrate is diluted in buffer to a protein concentration at least 20% but less than 40% greater than that utilized in conventional Western Blot. Preferably, the antigen concentrate is diluted in buffer to a protein concentration of about 60 to 120 ug per 10×16 cm gel. The preferred buffer is 0.05M TRIS-HCl/50% glycerol, pH 8, 2.5% SDS (sodium dodecyl sulfate) and 5% mercaptoethanol. Other buffers known to those skilled in the art are also suitable, such as 9M urea in 0.01M TRIS-HCl.

As noted above, the protein concentration of the antigen lysate used with the method of the invention is approximately 20 to as much as 40% higher than the 50–100 ug/10×16 cm gel typically used for conventional Western Blot. See pages 380 to 381 of the guidelines published by Tsang V. C., J. Peralta, R. Simons, In: Methods of Enzymology, vol. 92, Chapter 29, 1983, Academic Press Inc., which sets forth the 5–10 ug/8×10 cm gel workable range of protein concentrations used in the conventional Western Blot assay.

The antigen is generally first denatured by boiling, typically for about 5 minutes. Then, the denatured antigen is subjected to conventional gel electrophoresis of the type reported by Tsang et al, Methods in Enzymology, vol. 92 (1983).

A tracking dye is preferably added to the diluted antigen to produce visible protein banding. The preferred dye is bromophenol blue. The dye is preferably prepared by dissolving 50 mg bromophenol blue in 8 ml of glycerol, plus 1 ml each of 0.5M TRIS-HCl at pH 8.0 and H₂O. Other dyes, known to those skilled in the art, may also be used.

Suitable gels for the electrophoresis are also prepared in accordance with the method of Tsang et al., Methods in Enzymology, vol. 92 (1983). A 10% resolving polyacrylamide gel with a 3% stacking gel (SDS-PAGE) is preferred because it resolves a molecular weight range of 12,000-160,000, thus embracing the proteins within the HIV-I viral lysate. However, a gradient SDS-PAGE gel can also be used. For example, a gradient ranging from 3.3%-20% polyacrylamide gel resolves the antigen in the desired molecular weight range. Preferably, a molecular weight marker is electrophoresed together with the HIV-I antigen. These marker materials serve to calibrate the gels and facilitate identification of the protein bands of specific molecular weights. Suitable molecular weight markers are commercially available, such as a Cytochrome C molecular weight system from United States Biochemical Corporation.

Electro-Transfer Of The Resolved Antigen

Subsequent to electrophoresis, the protein bands of the resolved antigen are electro-transferred preferably to nitrocellulose sheets, (e.g., those commercially available from Schleicher and Schuell, Inc. as Item no. BA 83, which is a roll of nitrocellulose paper having a 0.2 micron pore size). Other types of papers, known to those skilled in the art, such as diazo-type paper are also suitable. The electro-transfer of the protein bands is accomplished by means of the technique reported by Tsang et al., Methods in Enzymology, vol. 92, particularly page 378, and W. Van Raamsdonk, et al. J. Immunol. Methods 17:337 (1977).

In accordance with the present invention, the resolved HIV-I protein is incubated in the presence of milk proteins, preferably defatted proteins. (The presence of fat interferes with the test.) Suitable defatted milk proteins included Carnation ® lowfat milk powder, but any defatted milk proteins as may be known are also useful. Such milk proteins are known to constitute about 60 to 90% casein, a phosphoprotein rich in serine; and from 10 to 40% of various other proteins including lactoalbumin, lactoglobulin, membrane globulin and a small amount of alkaline phosphatase, peroxidase catalase and xanthine dehydrogenase. The milk proteins may be introduced into the assay system in one of several ways.

According to a first embodiment of the invention, the nitrocellulose paper blotted with the resolved HIV-I antigen protein is coated with the milk proteins from a solution of buffer (e.g., PBS-Tween 20), containing about 5 to 10% milk proteins for about 60 minutes. The nitrocellulose paper is subsequently dried at room temperature for a period of 30-60 minutes. After evaporation, the paper is washed in the buffer solution not containing milk proteins (e.g., PBS-Tween 20) at room temperature for 1-5 minutes. The treated paper is then stored under humid conditions until use.

According to a second embodiment of the invention, the milk proteins are thoroughly mixed with and dissolved in the buffer solutions containing the test sample and controls. The controls and serum samples are then incubated with the nitrocellulose strips for 15 to 20 minutes. The liquid of each tube is discarded and the strips are washed with a PBS-Tween buffer at pH 7.3-7.4. The washing cycle consists of four 1 minute washings.

According to a third embodiment of the invention, the milk proteins are precoated on the nitrocellulose strips and additionally mixed with and dissolved in the buffer solution.

The nitrocellulose sheets are then cut into strips approximately 2-2.5 mm in width. Each strip, after appropriate labelling, is placed in a separate test tube or in aluminum foil for determination of antibodies to HIV-I viral lysate by the enzyme linked immunoassay of the invention. The nitrocellulose strips can also be placed in incubation trays for in house testing. It should be understood, however, that an uncut sheet can be placed in an incubation tray equipped with a pressing cover rather than cut into individual strips. This technique is also well-suited to in-house as opposed to on site testing. As can be appreciated, however, on site testing is facilitated by use of individual tubes. Also, placing the strips in individual tubes minimizes the need for handling during the assay procedure and thus, possible smearing of the fragile protein patterns with fingerprints. Using strips is also more economical than uncut sheets because less reagent is necessary to carry out the test.

Test samples, positive and negative references and reagent controls are added to the tubes containing the nitrocellulose strips blotted with resolved antigen. Test samples include, but are not limited to serum, semen and other body fluids. The positive reference is typically a sample known to contain antibodies to the HIV-I viral lysate. Positive references have been obtained from the Centers for Disease Control (CDC), Atlanta, Ga. Alternatively, a positive reference may be made from any sample which has been standardized with a positive reference obtained from the CDC. Standardization typically means that the same test results were obtained in about 20 runs. The positive reference is diluted 1/200 (1 part positive reference to 200 parts buffer) in PBS (phosphate buffered solution)-Tween, pH 7.2-7.4. Typically, 15 ul of the positive reference is mixed with 3 ml PBS-Tween.

The negative control is a sample known to be devoid of antibodies to HIV-I viral lysate, and is prepared by diluting 1/20 with PBS-Tween, pH 7.2-7.4. Typically, 150 ul of a negative reference is mixed with 3 ml PBS-Tween. Negative references have also been obtained from the CDC.

As the assay method of the invention is a qualitative rather than quantitative determination, the positive and negative references are used to evaluate the test results by comparison with the results obtained for test samples.

The reagent control is included as a quality control feature of the present invention and is used to assure accurate functioning of the test. Normally, the reagent control is the buffer used to dilute test samples and controls. Preferably, PBS-Tween, pH 7.2-7.4 is used as the reagent control. However, the reagent control is not necessary during routine readings of the strips.

As indicated hereinabove, employing the milk protein treatment of the present invention, test samples may be used which are more concentrated than those used in conventional Western Blot, to accelerate the binding of antibodies to HIV-I viral lysate to the antigen contained in the strips. Typically, test samples are about three to five times more concentrated than samples tested by the Western Blot assay. On the other hand, test samples used in accordance with the present invention, need to be about 2.5 times less concentrated than the samples employed in the Quick Western Blot assay. The present method thus provides increased sensitivity, without markedly increased non-specific protein binding such as may occur employing very large test sample concentration.

For serum samples, three to seven times the concentration utilized in the conventional Western Blot assay is required, i.e., a dilution of one part serum to twenty parts buffer as compared to the 1:100 dilution factor used in the western Blot assay. (See Tsang et al., Method of Enzymology, vol. 92, 1983.) Theoretically, the actual dilution factor for particular samples may be varied, however, depending upon whether a specimen gives an extremely weak positive response. Studies indicate that five times the serum concentrations normally used with conventional Western Blot are unsuitable because the high amount of serum proteins, other than the antibodies being evaluated, interfere with the test. A PBS-Tween, pH 7.2–7.4 buffer is preferred for the dilution of samples. Typically, 60 ul of a serum sample is mixed with 3 ml of PBS-Tween. But other known buffers may be substituted.

The strips are then incubated with the positive and negative references, controls and test samples at room temperature, preferably for about 10 to 20 minutes, to permit the binding of any antibodies to HIV-I present in the sample to the antigen in the nitrocellulose strips. A 20 minute incubation period is particularly preferred to insure optimum binding of weak positives.

Incubation With The Enzyme-Conjugated Antiserum

The liquid content of each tube is discarded, with the strips remaining in place in the tubes. The strips are then washed, preferably with PBS-Tween buffer at pH 7.3. In particular, the washing cycle includes four 1 minute washings with PBS-Tween. The strips are then incubated with an enzyme-conjugated anti-human IgG antiserum preferably for about 10 to 20 minutes, at room temperature, to permit binding of the enzyme conjugated antiserum to any antibody which bound to the antigen during the first incubation period. Preferably, goat anti-human IgG antiserum-horseradish peroxidase conjugate is employed, although other enzyme conjugated antisera as are known to those skilled in the art may be used. Again, a 20 minute incubation period is preferred.

Once more, the liquid content of each tube is discarded. The strips are then washed. Preferably the washing cycle includes four 1 minute washings with PBS-Tween followed by one 1 minute washing with PBS.

Incubation With An Enzyme Substrate

Then, the strips are incubated with an enzyme substrate (color change indicator) for about 10 minutes at room temperature, for production of a color. The appropriate substrate for use with horseradish peroxidase enzyme is 3,3' diaminobenzidinetetrahydrochloride dihydrate (DAB). It should be understood, however, that substrate selection is dictated by the enzyme used. After the incubation period, the color reaction is stopped by addition of distilled $H_2O$ and the results determined, according to standard techniques, as reported by Tsang, et al., Methods in Enzymology, vol. 92 (1983).

In accordance with the present invention, determination of the presence of antibodies to HIV-I can be accomplished in about 50–60 minutes because of the greatly reduced incubation times, totalling about 40 minutes, as compared with the Western Blot assay which requires at least 20 hours and the Quick Western Blot assay which takes 80 minutes.

The Diagnostic Test Kit

In accordance with a preferred embodiment of the invention, a self-contained diagnostic test kit is provided which permits "on site" screening for antibodies to HIV-I virus. The test kit includes a set of tubes containing positive and negative references and at least 1 buffer tube containing a predetermined volume of buffer to which the test sample is added in a predetermined amount to obtain a sample concentration from 3 to 7 times greater than that utilized in the Western Blot asay. The reference and control tubes are prediluted, and thus, the user need only dilute the test sample. A set of strip tubes is also provided, each tube containing a nitrocellulose strip containing resolved HIV-I antigen protein, electro-transferred from an SDS-PAGE gel loaded with from 20% to 40% higher antigen protein concentration than that used in conventional Western Blot. Preferably, the strips contain resolved HIV-I viral lysate, electrotransferred from an 10×16 cm SDS-PAGE gel loaded with from 61–96 ug of antigen protein compared to a range of 51–80 ug for Western Blot, depending upon the relative amount of specific HIV proteins.

As indicated hereinabove, the milk protein additive is either pre-dissolved in the buffer solutions containing the test sample and the positive and negative references, or coated on the nitrocellulose strips containing the resolved HIV-I antigen protein. Alternatively, the milk proteins may be separately provided in powder form to be added to the buffer by the user; the resulting buffer solution can then be directly mixed with the test and reference samples, or used to coat the test strips.

In a preferred embodiment, the reference, control and sample tubes are numbered. The strip tubes are assigned numbers corresponding to those on the reference control and sample tubes. The strips are assigned numbers corresponding to the tubes in which they are placed. This type of numbering system avoids inadvertent mix-ups which can destroy the accuracy of the assay. As can be appreciated, if the top of a tube containing a positive sample is placed on a tube containing a negative sample, it is likely to obtain a false positive result.

The kit also contains vials of enzyme-conjugated antiserum reagent, substrate or color change indicator, two washing buffers and solution for terminating the color reaction. Preferably, goat anti-human IgG antiserum-horseradish peroxidase is used as the enzyme conjugated anti-serum reagent. The preferred substrate, reaction terminating agent and washing buffers are DAB, distilled $H_2O$, and PBS Tween and PBS, respectively.

Preferably, pre-developed positive and negative reference strips and reagent control strips are provided in the kit. These controls are prepared in substantially the same manner as previously described except that after developing, the strips are air dried. The predeveloped strips are used to evaluate the test results by a visual comparison with the test strips after completion of a color reaction. The reagent control as noted, is provided to assure the accurate functioning of the reagents. The predeveloped reference and control strips are a significant feature of the present invention because they facilitate reading the assay results and practically eliminate the need for a skilled technician to evaluate the results.

Also, as the kit is self-contained, no laboratory equipment is needed. The advantages of such a kit are apparent, as it facilitates screening for HIV-I antibodies at any time and virtually at any place, including remote geographic areas and those locations lacking a 24 hour testing facility. As aforementioned, this is of utmost importance in certain organ transplantation situations.

It has been reported that with HIV-I infection the major immune reactivity is directed to gp41, a 41,000 molecular weight protein and especially gp120 and gp160, 120,000 and 160,000 molecular weight proteins, respectively, which are proteins believed to be envelope proteins of the virus. Thus, gp41, gp120 and/or gp160 bands are of critical significance in the present method. Also of importance is gp24, a 24,000 molecular weight protein. Typically, the test is considered positive if activity is recorded at the gp24 and gp41 bands and/or the gp120 and/or gp160 bands. Accordingly, proper resolution of the HIV-I antigen lysate is vital. The amount of protein subjected to electrophoresis is related to the distinctiveness of the resulting bands. Obviously, it is desirable to obtain distinct banding at the critical points, particularly gp120, gp160 and gp41 as well as gp24 with few or no noise bands. The method of present invention results in better resolution of the important gp160 and gp120 bands than either of the conventional and Quick Western Blot techniques. The presence of these higher molecular weight proteins provide a more accurate indication of the presence of the AIDS retrovirus in the tested sample since these envelope proteins are considered to be the most reliable bands in the evaluation of the test strips.

The protein bands are much clearer and better resolved in the present invention as compared to the other Western Blots, resulting in greater ease in interpreting the results.

FIGS. 1 and 2 represent the results of a test comparing the resolution of viral protein obtained by Quick Western Blot and Quick Western Blot II, respectively. As can be seen, better resolution of the various protein bands is obtained by following the present method; the protein bands are clearer and consequently greater ease in interpreting test results is achieved.

The following specific examples of the Quick Western Blot II Assay and its use of milk proteins are further illustrative of the nature of the present invention, although it is understood that the invention is not limited thereto.

FIG. 1

Quick Western Blot 1 (OWB1)

Strip #1: Positive Control
Strip #3: Negative Control
Strip #2 & 4: Serum specimens
The assay was conducted in accordance the method set forth in copending U.S. patent application Ser. No. 871,505. The SDS-PAGE gel/ 10×16 cm was loaded with 76.5 ug HIV lysate and the total reaction time was 70 minutes.

FIG. 2

Quick Western Blot 2 (QWB2 OR RapWB)
Strip #1: Positive Control
Strip #2: Negative Control
Strip #3 & 7: Serum specimens The assay was conducted in accordance with the method described herein. The SDS-PAGE gel was loaded with appr. 67 ug of HIV lysate. The milk protein was precoated on the nitrocellulose strips and added to the buffer containing the samples. The total reaction time was 40 minutes. (Note that the viral lysate used in each of the assays reported in FIGS. 1 and 2 were obtained from different batches.)

EXAMPLE I

The Quick Western Blot II Assay, Dissolving the Milk Proteins in the Buffer Solutions HIV-I antigen concentrate was electrophoretically resolved in the molecular weight range of 12,000–160,000.

The HIV lysate antigen was electro-transferred to nitrocellulose paper. The paper was then cut into strips and placed in separate test tubes.

0.15 g of Carnation ® milk protein powder was dissolved in each 3 ml buffer solution containing the sample and controls, by turning end over end for 5-10 times to allow complete mixing with the milk proteins. The controls and serum samples were then incubated with the nitrocellulose strips for 15 minutes. The liquid of each tube was discarded and the strips were washed with PBS-Tween buffer at pH 7.3-7.5. The washing cycle consisted of four 1 minute washings.

The strips were then incubated with an enzyme conjugated anti human IgG antiserum (1:500) for 15 minutes at room temperature. The liquid was again discarded and the strips were washed four times with PBS-Tween followed by a one minute washing with PBS alone.

The strips were incubated for 10 minutes with horseradish peroxidase and its substrate 3,3' diaminobenzidinetetrahydrochloride dihydrate (DAB). The color reaction was stopped by the addition of distilled $H_2O$ and the results were evaluated by comparing the test strips with the pre-developed positive, negative and reagent strips provided with the kit, and the assay was completed within 50 minutes of the initial treatment of the test sample.

EXAMPLE II

The Quick Western Blot II Assay, Coating the Antigen Bound Nitrocellulose Strips with Milk Protein HIV-I antigen concentrate corresponding to 61 ug/10×16 cm gel was electrophoretically resolved in the molecular weight range of 12,000–160,000.

The HIV lysate antigen was electro-transferred to nitrocellulose paper. The paper was then coated in a bath equipped with magnetic stirring with a PBS-Tween 20 buffer solution containing nonfat milk proteins.

The PBS-Tween buffer contained 5% Carnation ® milk proteins. This was achieved by mixing 5g of the powder with 100 ml of the buffer.

The nitrocellulose paper was subsequently dried at room temperature for a period of 5-30 minutes. After evaporation, the paper was washed in PBS-Tween-20 at room temperature for 2 minutes. The strips were then stored under humid conditions until use.

The procedure of Example I was then followed beginning with the initial incubation of the nitrocellulose strips.

A study was performed comparing the QWB II method described herein with the conventional Western Blot and ELISA techniques. The results of the tests run on 338 serum samples is reported in Table I. As shown in Table I, the QWB II assay method of the present invention is as reliable as the conventional Western Blot assay. In fact, at least one sample which was inconclusive using the Western Blot was shown to be positive using the Quick Western Blot II Assay. The advantages of the Quick Western Blot II are apparent.

The presence of antibodies to HIV-I can be detected in 50 minutes. The rapidity with which the test can be performed is enormously important to organ transplant recipients, since donated organs have a limited usable life span outside the body, and in trauma cases where immediate surgery is needed. The Quick Western Blot II, through the use of milk proteins, results in both enhanced and accelerated specific protein binding. Furthermore, less unspecific binding of proteins occur. The certainty with which the specific bands can be detected facilitates the diagnosis of AIDS and probably also the provides useful information as to the stage of the HIV infection antibodies to different molecular weight antigen proteins may be indicative of various stages in the progression of the disease. Table II provides information about correlating the presence of specific protein bands with various stages in the progression of the disease.

Additionally, and apart from the organ donor situation, utilizing the method and diagnostic test kit of the invention, hospitals can obtain fast and accurate results on patients suspected of HIV-I infection, and thus expedite treatment. Moreover, if AIDS is diagnosed, hospital personnel can more readily adopt necessary precautions and minimize accidental viral contamination.

While preferred embodiments of the invention have been described, it will be apparent to those of ordinary skill in the art that various changes and modifications may be made therein without departing from the spirit and scope of the invention. Accordingly, the above description should be construed as illustrative, and not in a limiting sense, the scope of the invention being defined by the following claims.

TABLE I

Study Comparing Conventional Western Blot and ELISA with Quick Western Blot II

|  | HIV Ab ELISA | HIV Ab WB | HIV Ab QWB2 |
|---|---|---|---|
| POSITIVE FOR ANTIBODY | 208 | 120 | 130 |
| INCONCLUSIVE RESULTS | — | 12 | 11 |
| NEGATIVE RESULTS | 130 | 197 | 197 |

338 serum specimens obtained from Baylor University Medical Center and from various Laboratories in the Dallas Ft. Worth Metroplex Area, were tested for the presence of antibodies to HIV-I with ELISA screening with Behring Processor 2 for HIV antibody using Electronucleonic HIV Ab Test kits, with Quick Western Blot 2 (QWB2 or RapWB) and with confirmatory conventional Western Blot technique. The QWBII was performed in accordance with the method described herein. The milk proteins were precoated on the nitrocellulose strips and mixed into the buffer solutions containing the samples and controls.

TABLE II

HIV Antigen/Antibody Rapid Western Blot Patterns (Correlation with Stage and Prognosis)

| CLINICAL STAGE | TEST RESULTS |
|---|---|
| Acute Infection | HIV Antigenemia (First) IgM Antibodies to HIV (second) (ELISA Negative) IgG Anti p24/55 & gp160/120 (Third) (In some cases ELISA Negative in the start) IgG Anti gp41 (Fourth) |
| Dormant but still Infective (after 1 to 2 months following infection) | HIV Antigenemia variable IgM Antibodies often present within 1. month after infection (ELISA Negative) |
| AIDS and pneumosystis | IgG anti p24/55 present IgG anti gp160/120 present IgG anti gp41 present IgG anti p64/53 present IgG anti Reverse Transcriptase present |
|  | HIV Antigenemia present IgG anti p 24/55 low or absent IgG anti gp41 low or absent IgG anti gp160 present at low levels IgG anti p53 low or absent IgG anti p64 present at low levels |
| Kaposi's Sarcoma | HIV Antigenemia present in many cases. IgG anti p24/55 low or absent IgG anti gp41 low or absent IgG anti gp120 present at low levels IgG anti gp160 present at low levels IgG anti gp53 present at low levels IgG anti p64 present at low levels |

Information for Table II was obtained from the following sources:
1. Pan, L-2, Cheng - Mayer, C., Levy, JA J. Infect. Dis. (155) 626–632 (1987).
2. Lelie, P. N., Van der Poel, C. L., Reesink, H.W. Lancet (I) p632 (1987).
3. Kumar, P., Pearson, J., Martin, D. H. et al. Ann Intern. Med. (106) 244–245 (1987).
4. Wall, R. A., Denning, D. W., Amos, A. Lancet (I) p566 (1987).
5. Weber, J. M., Clapham, P. R. Lancet (I) 119–122 (1987).

We claim:
1. In a method for the detection of antibodies to HIV-I retrovirus, comprising:
   (a) contacting nitrocellulose paper containing blotter resolved HIV-I antigen protein obtained from gel electrophoretically resolved HIV-I viral lysate with a test sample diluted with a buffer, and incubating the nitrocellulose paper and test sample to permit binding of antibodies present in the sample to the protein on the nitrocellulose paper;
   (b) contacting the incubated nitrocellulose paper of step (a) with an enzyme conjugated antiserum reactive with said antibodies, and incubating to permit binding of the antiserum to said antibodies;
   (c) contacting the incubated nitrocellulose paper of step (b) with an enzyme substrate specific for the enzyme of step (b), and incubating to thereby produce color;

(d) stopping the color producing reaction of step (c); and (e) evaluating the amount of color produced as an indication of the presence of antibodies to HIV-I viral lysate;

the improvement wherein (1) the viral lysate is electrotransferred to the nitrocellulose paper in a concentration at least 20%, but less than 40%, greater than the 50–100 ug of HIV-I antigen protein per 10×16 cm electrophoresis gel utilized in the Western Blot assay;

(2) the resolved HIV-I antigen protein is incubated in step (a) in the presence of milk protein; and (3) the test sample is diluted in buffer to a serum concentration at least 3, but less than 7, times greater than the 1:100 dilution of the test sample utilized in the Western Blot assay, to complete the assay within 60 minutes.

2. The method of claim 1, wherein said milk protein comprises from 60 to 90% by weight casein, and from 10 to 40% by weight of a material selected from the group consisting of lactoglobulin, membrane globulin, alkaline phosphatase, peroxidase catalase, xanthine dehydrogenase, and mixtures thereof.

3. The method of claim 1, wherein the nitrocellulose paper containing the blotted resolved HIV-I antigen is coated with milk protein prior to incubation with the test sample in step (a).

4. The method of claim 1, wherein the milk protein is mixed with the buffer used to dilute said test sample.

5. The method of claim 1, wherein said antigen lysate has a protein concentration of between 60–100 ug per 10×16 cm gel.

6. The method of claim 1, wherein said test sample is serum.

7. The method of claim 1, in which step (a) is repeated with at least one positive control (a sample containing HIV-I antibodies) and one negative control (a sample that is devoid of HIV-I antibodies) in place of the test sample, the reaction product formed thereby is subjected to steps (b-e), and the colors produced are compared as standards with the color produced from the test sample, to evaluate the presence of antibodies to the HIV-I retrovirus in the test sample.

8. In a method for the detection of antibodies to HIV-I retrovirus, comprising:

(a) electrophoretically resolving HIV-I antigen protein from a viral lysate;

(b) electrotransferring the resolved antigen onto nitrocellulose paper;

(c) incubating the blotted nitrocellulose paper with a test sample diluted with buffer;

(d) incubating the reaction product formed in step (c) with an enzyme conjugated antiserum;

(e) incubating the reaction product formed in step (d) with an enzyme substrate, said substrate being specific for the enzyme reacted in step (d), to produce color;

(f) stopping the color producing reaction of step (e); and (g) evaluating the amount of color produced in step (e) as an indication of the presence of antibodies to the HIV-1 viral lysate;

the improvement comprising:

(1) treating the HIV-I antigen with milk protein by
(i) coating the blotted nitrocellulose paper produced in step (b) with 3% to 10% mil protein, or (ii) incorporating from 3% to 10% milk protein in the buffer utilized in step (c); and (2) reacting the viral lysate and the test sample in concentrations of viral lysate at least 20% but less than 40% greater than the 50–100 ug HIV-I antigen protein per 10×16 cm electrophoresis gel utilized in the Western Plot assay and serum concentrations from the test sample at least 3 but less than 7 times greater than the 1:100 dilution of the test sample utilized in the Western Blot assay; thereby enhancing and accelerating specific binding of the HIV-I antibody proteins to complete the assay within 60 minutes.

9. The method of claim 8, in which step (a) is repeated with at least one positive control (a sample containing HIV-I antibodies) and one negative control (a sample that is devoid of HIV-I antibodies) in place of the test sample, the reaction product formed thereby is subjected to steps (b-e), and the colors produced are compared as standards with the color produced from the test sample, to evaluate the presence of antibodies to the HIV-1 retrovirus in the test sample.

10. The method of claim 8, wherein the test sample is mixed with a buffer selected from the group consisting of PBS-Tween, TRIS buffers, TBS buffers, urea buffers, and polyethylene glycol in saline or distilled water.

11. In a method for the detection of antibodies to HIV-I retrovirus, comprising:

(a) contacting nitrocellulose paper containing blotter resolved HIV-I antigen protein obtained from gel electrophoretically resolved HIV-I viral lysate with a test sample diluted with a buffer, and incubating the nitrocellulose paper and test sample to permit binding of antibodies present in the sample to the protein on the nitrocellulose paper;

(b) contacting the incubated nitrocellulose paper of step (a) with an enzyme conjugated antiserum reactive with said antibodies, and incubating to permit binding of the antiserum to said antibodies;

(c) contacting the incubated nitrocellulose paper of step (b) with an enzyme substrate specific for the enzyme of step (b), and incubating to thereby produce color;

(d) stopping the color producing reaction of step (c); and (e) evaluating the amount of color produced as an indication of the presence of antibodies to HIV-I viral lysate;

the improvement wherein (1) the viral lysate is electrotransferred to the nitrocellulose paper in a concentration at least 20%, but less than 40%, greater than the 50–100 ug of HIV-I antigen protein per 10×16 cm electrophoresis gel utilized in the Western Blot assay;

(2) the resolved HIV-I antigen protein is incubated in step (a) in the presence of milk protein; and (3) the test sample is diluted in buffer to a serum concentration at least 3, but less than 7, times greater than the 1:100 dilution of the test sample utilized in the Western Blot assay, (4) each incubation step is effected in no more than 20 minutes.

12. The method of claim 11, in which step (a) is repeated with at least one positive control (a sample containing HIV-I antibodies) and one negative control (a sample that is devoid of HIV-I antibodies) in place of the test sample.

13. In a diagnostic test kit for the detection of AIDS specific antibodies comprising
  (a) a set of control tubes comprising positive and negative reference;
  (b) at least one reagent control tube;
  (c) at least one dilution tube containing a predetermined volume of buffer for dilution of test samples;
  (d) a set of tubes containing nitrocellulose test strips containing resolved HIV-I antigen, said antigen being obtained from gel electrophoretically resolved HIV-I antigen lysate;
  (e) an enzyme conjugated antiserum for reacting with the antibody-antigen complex;
  (f) a color change indicator to ascertain whether the HIV-I antibodies are present; and
  (g) predeveloped positive and negative reference strips and reagent control strips for evaluating the results of the test by visually comparing the predeveloped strips with the test-strips after completion of a color change reaction;
the improvement comprising:
  (1) a milk protein reagent for binding with the resolved HIV-I antigen, said reagent being dissolved in the buffer in dilution tube (c) or coated on the nitrocellulose test strips in tubes (d);
  (2) the volume of buffer in dilution tube (c) being predetermined to obtain a concentration of test sample at least 3 but less than 7 times greater than the 1:100 dilution of the test sample utilized in the Western Blot assay; and
  (3) the resolved HI-I antigen on the nitrocellulose test strips in tubes (d) being present in a concentration at least 20% but less than 40% greater than the 50–100 ug of HIV-I antigen protein per $10 \times 16$ cm electrophoresis gel utilized in the Western Blot assay.

14. The diagnostic test kit of claim 13, wherein the electrophoretically resolved antigen has a concentration of 60 to 100 ug HIV protein/$10 \times 16$ cm gel.

15. The diagnostic test kit of claim 13 wherein the dilution tube contains 3 to 10% nonfat milk proteins.

16. The diagnostic test kit of claim 14 wherein the nonfat milk proteins comprise from 60 to 90% by weight casein, and from 10 to 40% by weight of a material selected from the group consisting of lactoglobuline, membrane globuline, alkaline phosphatase, peroxidase catalase, xanthine dehydrogenase, and mixtures thereof.

* * * * *

UNITED STATES PATENT AND TRADEMARK OFFICE
CERTIFICATE OF CORRECTION

PATENT NO. : 4,885,235
DATED : December 5, 1989
INVENTOR(S) : KURT B. OSTHER et al.

It is certified that error appears in the above-identified patent and that said Letters Patent is hereby corrected as shown below:

Column 9, line 17:  Change "gp24" to --p24--.

Column 9, line 19:  Change "gp24" to --p24--.

Column 9, line 26:  Change "gp24" to --p24--.

Column 9, line 53:  Change "(OWB1)" to --(QWB1)--.

Column 12, line 41: Change "gp53" to --p53-.

Column 12, line 54: In claim 1, change "blotter" to --blotted--.

Column 13, line 67: In claim 8, change "mil" to --milk--.

Column 14, line 29: In claim 11, change "blotter" to --blotted--.

Column 16, line 19: In claim 16, change "claim 14" to --claim 15--.

Signed and Sealed this

Twenty-third Day of February, 1993

*Attest:*

STEPHEN G. KUNIN

*Attesting Officer*  *Acting Commissioner of Patents and Trademarks*